United States Patent [19]

Lee et al.

[11] Patent Number: 5,498,726

[45] Date of Patent: Mar. 12, 1996

[54] PREPARATION OF PHYSOSTIGMINE CARBAMATE DERIVATIVES FROM PHYSOSTIGMINE

[75] Inventors: George E. Lee, Somerville; Thomas B. K. Lee, Whitehouse Station; Donna M. Borek, Clifton, all of N.J.

[73] Assignee: Hoechst-Roussel Pharmaceuticals Incorporated, Somerville, N.J.

[21] Appl. No.: 216,238

[22] Filed: Mar. 22, 1994

Related U.S. Application Data

[63] Continuation of Ser. No. 918,719, Jul. 21, 1992, abandoned.

[51] Int. Cl.$^6$ ................................................. C07D 487/00
[52] U.S. Cl. ................................................................ 548/429
[58] Field of Search ............................................... 548/429

[56] References Cited

U.S. PATENT DOCUMENTS

| | | | |
|---|---|---|---|
| 4,900,748 | 2/1990 | Brossi et al. | 548/429 |
| 4,914,102 | 4/1990 | Glamkowski | 514/411 |
| 4,978,673 | 12/1990 | Meroni et al. | 548/429 |
| 5,077,289 | 12/1991 | Glamkowski et al. | 548/429 |

FOREIGN PATENT DOCUMENTS 0253372  1/1988  European Pat. Off. .

*Primary Examiner*—Jacqueline Haley
*Attorney, Agent, or Firm*—Barbara V. Maurer

[57] ABSTRACT

This application relates to a new process for the preparation of a product of the formula

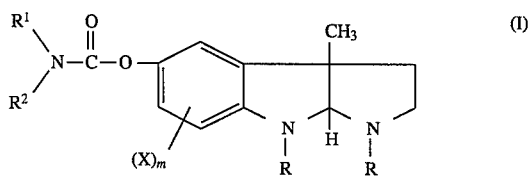

wherein R, $R^1$, $R^2$, X and m are as defined within, which process comprises preparing treating a compound such as physostigmine to form eseroline which is then treated with an appropriate compound or its equivalent. Acetic acid is added to the reaction mixture after the formation of eseroline.

25 Claims, No Drawings

PREPARATION OF PHYSOSTIGMINE CARBAMATE DERIVATIVES FROM PHYSOSTIGMINE

This is a continuation of a prior application Ser. No. 918,719, filed Jul. 21, 1992, now abandoned.

This application relates to a new process for the preparation of a product of the formula

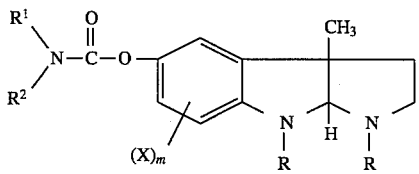

wherein

R is loweralkyl;

$R^1$ is hydrogen, loweralkyl, lowercycloalkyl, lowercycloalkylloweralkyl, lowerbicycloalkyl, aryl or aryllloweralkyl;

$R^2$ is loweralkyl, lowercycloalkyl, lowercycloalkylloweralkyl, lowerbicycloalkyl, aryl or arylloweralkyl; or $R^1$ and $R^2$ taken together with the nitrogen atom to which they are attached from a 3,4-dihydro-2(1H-isoquinoline group;

X is loweralkyl, loweralkoxy, halogen or trifluoromethyl; and m is 0, 1 or 2:

which process comprises (a) contacting a compound of formula II

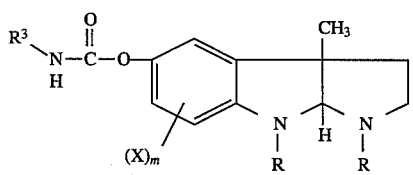

wherein R, X and m are as defined above and $R^3$ is loweralkyl, with base followed by a carboxylic acid of the formula $R^5COOH$ wherein $R^5$ is loweralkyl to afford a compound of formula III

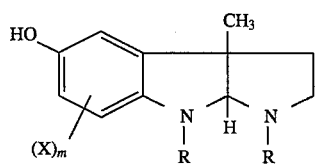

wherein R, X and m are as defined above;

(b) contacting the reaction mixture containing compound of Formula III either
  (1) with an isocyanate of the formula $R^2NCO$ and isolating a product of the formula I wherein $R^1$ is hydrogen; or
  (2) with a compound of formula IV

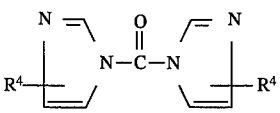

wherein $R^4$ is hydrogen or loweralkyl in the presence of a carboxylic acid of formula $R^5COOH$ wherein $R^5$ is as above to afford a compound of formula V

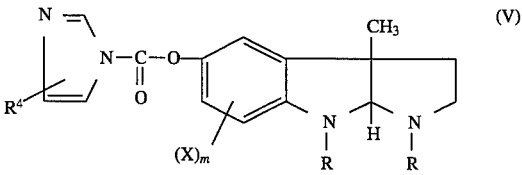

wherein R, $R^4$, X and m are as above;

contacting the reaction mixture containing compound of Formula V obtained in step (b) with a compound of the formula $R^1R^2NH$ wherein $R^1$ and $R^2$ are as above; and isolating the product of Formula I.

The products are useful as memory-enhancing and analgesic agents.

Unless otherwise stated or indicated, the term loweralkyl means a straight or branched alkyl group having from 1 to 6 carbon atoms. Examples of alkyl include methyl, ethyl, n-propyl, iso-butyl, pentyl, and hexyl.

Unless otherwise stated or indicated, the term cycloalkyl means a saturated ring containing 3 to 7 carbon atoms. Examples of cycloalkyl include cyclopropyl, cyclohexyl and cycloheptyl.

Unless otherwise stated or indicated, the term bicycloalkyl means a group having from 7 to 11 carbons.

Unless otherwise stated or indicated, the term halogen means fluorine, chlorine, bromine or iodine.

Unless otherwise stated or indicated, the term aryl means an unsubstituted phenyl or aromatic heterocyclic group; or a phenyl or aromatic heterocyclic group substituted with 1, 2 or 3 substituents each of which being independently loweralkyl, loweralkoxy, halogen, hydroxy, trifluoromethyl, phenoxy or benzyloxy.

Other methods for preparation of physostigmine carbamate derivatives are known. See for example Hamer U.S. Pat. No. 3,791,107 and Brufani, U.S. Pat. No. 4,831,155. However, there remains a need for higher yield and/or less costly means for obtaining these compounds.

The process of this invention provides a higher yield of the desired products. In a preferred embodiment it also provides for a more convenient "one-pot" process wherein the intermediates are not isolated, thus avoiding the expense and time of isolating the intermediate compounds.

In the reaction to form the compound of Formula III, it has been found that the reaction is advantageously carried out using a base such as an alkyllithium, for example, n-butyl lithium, preferably in an alkane solvent such as for example, a mixture of hexanes, or an alkali alkoxide, for example, potassium t-butoxide, preferably potassium t-butoxide. Generally, the reaction is carried out in an organic solvent such as tetrahydrofuran, dimethylformamide (DMF), 1,2-dimethoxyethane, 2-methoxyethyl ether, dioxane or diethylether, preferably tetrahydrofuran, at a temperature of from about 0° C. to about 50° C., preferably from about 10° C. to about 30° C.

There is added about one (1) equivalent of a loweralkyl carboxylic acid such as, for example, acetic acid to adjust the pH to from about 13 to about 8, preferably from about 9 to about 10, most preferably about 9.5.

Then there is added to the reaction mixture either an alkyl isocyanate or substituted alkyl isocyanate to form the compound of Formula I (wherein $R^3$ is hydrogen) or a carbamoylating agent such as carbonyldiimidazole to form the compound of Formula V.

In the case where an alkylisocyanate is added to form the compound of Formula I, the reaction is generally between about 0° C. and about 25° C., preferably about 5° C. to about 10° C. The reaction is monitored and the pH is maintained between about 9 and 10 by the addition of a base such as, for example, potassium t-butoxide or an acid such as, for example, acetic acid.

In the case where carbonyldiimidazole is added to form the compound of Formula IV, the addition is carried out at from about −30° C. to about 25° C., preferably at about −20° C. to −30° C., when potassium t-butoxide is used as base.

The reaction mixture containing the compound of Formula IV is then preferably acidified to from about 4 to about 6, more preferably to from about 4.5 to about 6, most preferably about 5.5, with an acid such as, for example, acetic acid, and an amine such as tetrahydroisoquinoline is added to give the compound of Formula I in good yields.

The addition of the amine is generally carried out from about −15° C. to about 25° C., preferably at from about −10° C. to about 20° C.

The free base starting material of Formula II such as physostigmine can be generated from its salt, such as from its salicylate salt by treatment with base such as sodium carbonate in a mixture of water and immiscible organic solvents such as, for example, dichloromethane, ethyl acetate or toluene and used in the process of the instant invention without further purification.

The following examples are for illustration purposes only and are not to be construed as limiting the invention. All temperatures are given in degrees centigrade (° C.) unless otherwise indicated.

EXPERIMENTAL

EXAMPLE 1

(3aS-cis )-
1,2,3,3a,8,8a-hexahydro-1,3a,8-trimethylpyrrolo-
[2,3-b]indol-5-yl
3,4-dihydro-2(1H)-isoquinolinecarboxylate To a solution of physostigmine (1 g) in dry THF (10 mL) at 10° C. under a nitrogen atmosphere was added with 2.5M n-BuLi in hexanes (1.5 mL) over 0.25 hour. After 0.5 hour at 20° C. the mixture contained a 2/98 HPLC ratio of physostigmine (II) and eseroline (III) as the Li phenoxide (pH-12). Addition of glacial HOAc (0.22g, pH-9.5) followed by 1,1'-carbonyldiimidazole (0.59 g) gave after 0.25 hour at 20° C. a mixture containing a 96/4 HPLC ratio of imidazolecarbonyl intermediate (V) and eseroline. Addition of 1,2,3,4-tetrahydroisoquinoline (0.6 mL, 1.3 equiv) gave after 0.5 hour at 25° C. a mixture containing (3aS-cis)-1,2,3,3a,8,8a-hexahydro- 1,3a,8-trimethylpyrrolo-[ 2,3-b]indol-5-yl 3,4-dihydro-2(1H)-isoquinolinecarboxylate and eseroline in a 75/25 HPLC ratio.

EXAMPLE 2

(3aS-cis-)-1,2,3,3a,8,8a-hexahydro-1,3a,8-
trimeththylpyrrolo-[2,3-b]indol-5-yl
3,4-dihydro-2(1H)-isoquinolinecarboxylate To a solution of physostigmine (1 g) in dry THF (10 mL) at 10° C. under a nitrogen atmosphere was added 2.5M n-BuLi in hexanes (1.5 mL) over 0.25 hour. After 0.5 hour at 20° C. the mixture contained a 2/98 HPLC ratio of physostigmine (II) and eseroline (III) as the Li phenoxide (pH−11.5). Addition of 1,1'-carbonyldiimidazole (0.59 g, 1.0 equiv) gave after 0.25 hour at 20° C. a mixture containing a 98/2 HPLC ratio of imidazolecarbonyl intermediate (V) and eseroline. Addition of 1,2,3,4-tetrahydroisoquinoline (0.6 mL, 1.3 equiv at pH=11.5) gave after 0.5 hour at 25° C. a mixture containing (3aS-cis)-1,2,3,3a,8,8a-hexahydro- 1,3a, 8-trimethylpyrrolo-[2,3-b]indole-5-yl 3,4-dihydro-2( 1H)-isoquinolinecarboxylate and eseroline in a 55/45 HPLC ratio.

EXAMPLE 3

(3aS-cis)
-1,2,3,3a,8,8a-hexahydro-1,3a,8-trimethylpyrrolo-
[2,3-b]indol-5-yl
3,4-dihydro-2(1H)-isoquinolinecarboxylate To a solution of physostigmine (6.88 g) in dry THF (69 mL) at 15° C. under a nitrogen atmosphere was added 2.5M n-BuLi in hexanes (10.5 mL) added over 0.25 hour. After 0.5 hour at 20° C. the mixture contained a 2/98 HPLC ratio of physosfigmine (II) and eseroline (HI) as the Li phenoxide (pH-11). Addition of glacial HOAc (1.5 mL, 1 equiv., pH=9.5) followed by 1,1'-carbonyldiimidazole (4.25 g, 1.05 equiv) gave after 1 hour at 20° C. a mixture containing a 99/1 HPLC ratio of imidazolecarbonyl intermediate and eseroline. Addition of glacial HOAc (7.15 mL, 5 equiv., pH=5) followed by 1,2,3,4-tetrahyclroisoquinoline (3.7 g, 1.1 equiv., added over 5 min) gave after 15 hour at 25° C. a mixture containing (3aS-cis)- 1,2,3,3a,8,8a-hexahydro-1, 3a,8-trimethylpyrrolo[2,3-b]indol-5-yl 3,4-dihydro-2(1H)-isoquinolinecarboxylate and eseroline in a 96/4 HPLC ratio.

EXAMPLE 4

(3aS-cis )-1,2,3,3a8,8a-hexahydro-1,3a
,8-trimethylpyrrolo-[ 2,3-b]indol-5-yl
3,4-dihydro-2(1H)-isoquinolinecarboxylate To a solution of physostigmine (68.8 g) in dry THF (690 mL) at 15° C. under a nitrogen atmosphere was treated with 2.5M n-BuLi in hexanes (102 mL) added over 0.25 hour, aged 0.5 hour at 15° C., then treated with glacial HOAc (14.6 mL, 1 equiv., pH−10) to give a mixture containing physostigmine (II) and eseroline (III) in 1/99 HPLC ratio. Addition of 1,1'-carbonyldiimidazole (44.6 g, 1.1 equiv.) gave after 1 hour at 20° C. a mixture of imidazolecarbonyl intermediate (V) and eseroline in a 89/1 HPLC ratio. Addition of glacial HOAc (85.9 mL, 6 equiv., pH=5) followed by 1,2,3,4-tetrahydroisoquinoline (37 g, 1.1 equiv. added over 5 min) gave after 15 hour at 25° C. a mixture containing (3aS-cis)-1,2,3,3a,8,8a-hexahydro- 1,3a,8-trimethylpyrrolo-[2,3-b]indol-5-yl 3,4-dihydro-2(1H)-isoquinolinecarboxylate and eseroline in a 98/2 HPLC ratio.

EXAMPLE 5

(3aS-cis)-1,2,3,3a,8,8a-hexahydro-1,3a,8-trimethyipyrrolo-[2,3-b]indol-5-yl 3,4-dihydro-2(1H)-isoquinolinecarboxylate To a solution of physostigmine (2.75g) in dry THF (28 mL) at 25° C. under a nitrogen atmosphere was added KOtBu (1.28 g) over 0.25 hour. The mixture was kept at 25° C. for 0.5 hour and then treated with glacial HOAc (0.6 mL, 1 equiv., pH=10) to give a mixture containing physostigmine (II) and eseroline (HI) in a 1/99 HPLC ratio. Addition of 1,1'-carbonyldiimidazole (1.92 g, 1.2 equiv) in 1.0, 0.05, 0.05 and 0.1 equiv. portions at 0.25 hour intervals at 20° C. gave after 10 min following each addition the following HPLC ratio of imidazolecarbonyl intermediate (V) and eseroline: 95/5, 96/4, 97/3 and 98/2. Addition of glacial HOAc (3.4 mL, 6 equiv., pH=5) followed by 1,2,3,4-tetrahydroisoquinoline (1.6 g, 1.2 equiv., added over 0.5 hour at 15° C.) gave after 15 hour at 25° C. a mixture containing (3aS-cis)-1,2,3,3 a,8,8a-hexahydro- 1,3a,8-trimethylpyrrolo-[2,3-b]indol-5-y13,4-dihydro- 2(1H)-isoquinolinecarboxylate and eseroline in a 97/3 HPLC ratio.

EXAMPLE 6

(3aS-cis)-1,2,3,3a,8,8a-hexahydro-1,3a,8-trimethylpyrrolo-[ 2,3-b]indol-5-yl 3,4-dihydro-2(1H)-isoquinolinecarboxylate To a solution of physostigmine (2.75 g) in dry THF (28 mL) at 25° C. under a nitrogen atmosphere was treated with KOtBu (1.28 g), added over 0.25 hour, aged 0.5 hour at 25° C., then treated with glacial HOAc (0.6 mL, 1 equiv., pH=10) to give a mixture containing physostigmine (II) and eseroline (III) in a 1/99 HPLC ratio. Addition of 1,1'-carbonyldiimidazole (1.7 g, 1.05 equiv) added in 1.0 and 0.05 equiv. portions at 1.25 hour intervals at −20° C. gave after 1.0 hour following each addition the following HPLC ratio of imidazolecarbonyl intermediate (V) and eseroline: 97/3 and 99/1. Addition of glacial HOAc (3.4 mL, 6 equiv., pH=5) followed by 1,2,3,4-tetrahydroisoquinoline (1.5 g, 1.1 equiv., added over 0.5 hour at 15° C.) gave after 4 hours at 25° C. a mixture containing (3aS-cis)-1,2,3,3a,8,8a-hexahydro- 1,3a,8-trimethylpyrrolo[2,3-b]indol-5-yl 3,4-dihyclro-2( 1H)-isoquinolinecarboxylate and eseroline in a 98/2 HPLC ratio.

EXAMPLE 7

(3aS-cis)-1,2,3,3a,8,8a-hexahydro-1,3a,8-trimethylpyrrolo-[2,3-b]indol-5-yl 3,4-dihydro-2(1H)-isoquinolinecarboxylate To a solution of physostigmine (290 g) in dry THF (2.3 L) at 15° C. under a nitrogen atmosphere was treated with KOtBu ( 126.4 g), added over 0.05 hour. The mixture was kept at 15° C. for 0.5 hour, then treated with glacial HOAc (64.1 mL, 1 equiv., pH=10) to give a mixture containing physostigmine (II) and eseroline (III) in a 1/99 HPLC ratio. Addition of 1,1'-carbonyldiimidazole (195.8 g, 1.15 equiv) in 10 (0.1 equiv.) and 3 (0.05 equiv.) portions at −30° C. over 2 hours gave the following HPLC ratios of imidazolecarbonyl intermediate (V) and eseroline after 1.0, 1.1 and 1.15 equiv.: 92/8, 98/2 and 99/1. Addition of glacial HOAc (482 mL, 8 equiv., pH=5) followed by 1,2,3,4-tetrahydroisoquinoline (175 g, 1.25 equiv., added over 1.5 hours at −10° C.) and warming to 20° C. for 15 hours gave a mixture containing (3aS-cis)- 1,2,3,3a,8,8a-hexahydro- 1,3a,8-trimethylpyrrolo-[ 2,3-b]indol-5-yl 3,4-dihydro-2(1H)-isoquinolinecarboxylate and eseroline in a 99/1 HPLC ratio. Addition of water (500 mL), cooling to −10° C., partial neutralization to pH=8 with 50% NaOH (471 g, 0.7 equiv based in HOAc), concentration of the THF under 30° C., toluene extraction (1×1L and 2×0.5L) of the residue, washing with water (500 mL), 5% NaCl (500 mL) and concentration under reduced pressure at 50° C. gave 370 g of crude product. This material was further purified by silica gel chromatography using ethyl acetate/methanol to give 346 g of 99% pure product in 89% yield from physostigmine. Recrystallization from methanol/water gave 321 g of crystalline product in 99% PHLC purity and 84 % yield.

EXAMPLE 8

Conversion of Physostigmine Salicylate to Physostigmine Free Base

To a heterogeneous mixture of physostigmine salicylate (450 g) in dichloromethane (1.35L) and water (1.35L) was added $Na_2CO_3$ (150 g) over 0.5–1.0 hour while maintaining 18°–20° C. During the addition the pH of the aqueous phase increases from 5.5 to 9.5. After stirring at 18°–20° C. for 0.5 hour the aqueous phase was separated and extracted with dichloromethane (2×112 mL). The combined dichloromethane phase was treated again with water (500 mL) and $Na_2CO_3$ (23 g) at 18°–20° C. and stiffed for 0.5 hour. The aqueous phase was separated, extracted with dichloromethane (2×112 mL) and the combined dichloromethane phases were washed with water (450 mL), dried over $K_2CO_3$ (20 g) and concentrated under reduce pressure below 30° C. to give 302 g of crystalline physostigmine free base (100.8% of theory, 99.0% HPLC purity).

EXAMPLE 9

(3aS-cis) -1,2,3,3a,8,8a-hexahydro-1,3a,8-trimethyl-pyrrolo-[2,3-b]indol-5-ol, cyclohexylcarbamate ester Physostigmine (550 mg) and sodium methoxide (108 mg) are placed in a flask to which vacuum has been applied (5–10 mm Hg). Absolute ethanol (70 mL) is then added over 2 hours in small volumes, under agitation at an external temperature of 25° C. Following evaporation of the ethanol, benzene (50 mL) was added via septum and the mixture was again allowed to evaporate to dryness. The reaction mixture at this point contained physostigmine (II) and eseroline (HI) in a 12/88 HPLC ratio. To this residue was added benzene (50 mL) containing cyclohexyl isocyanate (0.5 g) and the mixture was kept at 25° C. After 3 hours the mixture contained physostigmine, eseroline and (3aS-cis)- 1,2,3,3a, 8,8a-hexahydro- 1,3a,8-trimethylpyrrolo-[ 2,3-b]indol-5-ol, cyclohexylcarbamate (ester) in a 11/61/28 HPLC ratio. Following acidification and workup the composition of the crude product remained unchanged.

EXAMPLE 10

(3aS-cis) -1,2,3,3a,8,8a-hexahydro-1,3a,8-trimethyl-pyrrolo [2,3-b ]indol-5-ol, 3-chlorophenyl carbamate ester To a solution of physostigmine (25 g) in dry THF (250 mL), maintained under nitrogen atmosphere at 25° C., was added KOtBu (11.5 g), added in portions over 0.25 hour while maintaining the temperature between 25°–30° C. After 0.5 hour the mixture was cooled to 5° C. and treated with glacial HOAc (6.0 mL, 1,1 equiv., pH=9.5) added over 0.25 hours. This mixture contained physostigmine (II) and eseroline (III) in a 1/99 PHLC ratio. 3-Chlorophenyl isocyanate (25.8 g) was added over 1 hour at 5° C. followed by the addition of KOtBU (5×0.05 equiv.) over 0.5 hour to maintain the pH between 9.5 to 10.0. The mixture contained eseroline and (3aS-cis)-1,2,3,3a,8,8a-hexahydro- 1,3a,8-trimethylpyrrolo[2,3-b]indol-5-ol, 3-chlorophenylcarbamate (ester) in a 1/99 HPLC ratio. The product (31.6 g) was isolated as the fumarate salt in 71.3% yield following water washing, concentration under reduced pressure, chromatographic purification on silica gel with ethyl acetate, and acification of the purified free base in ethyl acetate (300 mL) with fumaric acid (1 equiv.).

EXAMPLE 11

(3aS-cis)-1,2,3,3a,8,8a-hexahydro-1,3a,8-trimethyl-pyrrolo [2,3-b ]indol-5-ol, 3-chlorophen ylcarbamate (ester)

To a solution of physostigmine (10 g) in dry THF (100 mL), maintained under a nitrogen atmosphere at 25° C., was added KOtBu (4.4 g), added in portions over 0.25 hour while maintaining the temperature between 25°–30° C. After 0.5 hour the mixture was cooled to 5° C. and treated with glacial HOAc (2.5 mL, 1,2 equiv., pH=8.5). This mixture contained physostigmine (II) and eseroline (HI) in a <1/95 HPLC ratio. 3-Chlorophenyl isocyanate (5.6 g, 1 equiv.) was added at –5° C. over 5 minutes. After 0.25 hour the reaction mixture, at pH=7.0, contained eseroline, (3aS-cis)- 1,2,3,3a,8,8a-hexahydro- 1,3a,8-trimethylpyrrolo[2,3-b]indol- 5-ol, 3-chlorophenylcarbamate (ester) and side product (formed by pH dependant reversible addition of a second isocyanate residue to product) in a 39/3/39 HPLC ratio. Adjustment of the pH by addition of KOtBu (0.5 g, 0.1 equiv. to pH-8.5) changed the HPLC ratio to 12/50/5.

EXAMPLE 12

(3aS-cis)-[3aα,5(R*),8aα]]1,2,3,3a,8,8a-hexahydro-1,3a,8-trimethyl-pyrrolo[2,3-b]indol-5-yl, (1-phenylethyl)carbamate To a solution of physostigmine (55.1 g) in dry THF (600 mL), maintained under a nitrogen atmosphere at 10°–20° C., was added KOtBu (26.8 g), added in portions over 0.5 hour while maintaining the temperature between 10°–20° C. After 0.5 hour the mixture was cooled to 10° C. and treated with glacial HOAc (12.6 mL, 1,1 equiv., pH=9.5). This mixture contained physostigmine (II) and eseroline (III) in a 1/99 HPLC ratio. (S)-(–)-α-methylbenzyl isocyanate (29.0 g, 1 equiv) was added over 1.5 hours at 10° C. During the addition the pH of the reaction remained constant at 9.5. After 0.5 hour the mixture contained eseroline and (3aS-[3a-α,5(R*),8a-α]]-1,2,3,3a,8,8a-hexahydro- 1,3a,8-trimethyl-pyrrolo[2,3-b]indol-5-yl, (1-(phenyl)ethyl carbamate ester in a 2/98 HPLC ratio. The product (63 g) was isolated in 86% yield and 99.5% HPLC purity following water washing (300 mL), concentration of the THF phase, chromatographic purification on neutral alumina with dichloromethane (DCM) elution and recystallization from diisopropyl ether.

EXAMPLE 13

(3aS-[3a-α,5(S*),8a-α]]-1,2,3,3a,8,8a-hexahydro-1,3a,8-trimethyl-pyrrolo[2,3-b]indol-5-yl,(1-(phenylethylz)carbamate To a solution of physostigmine (55.1 g) in dry THF (600 mL), maintained under a nitrogen atmosphere at 8°–12° C., was added KOtBu (26.8 g), in portions over 0.5 hour while maintaining the temperature between 10°–18° C. After 0.5 hour the mixture was cooled to 5° C. and treated with glacial HOAc (12.6 mL, 1,1 equiv., pH=9.5). This mixture contained physostigmine (II) and eseroline (Ill) in a 1/99 HPLC ratio. (R)(+)-α-methylbenzyl isocyanate (29.0 g, 1 equiv) was added over 0.5 hour at 10° C. After 10 minutes following the addition of isocyanate at pH–10.0 the mixture contained eseroline and [3aS-[3a-α,5(S*),8a-α]]-1,2,3,3a,8, 8a-hexahydro- 1,3a,8-trimethyl-pyrrolo[2,3-b]-indol-5-yl, (1-phenylethyl)carbamate in a 3/97 HPLC ratio. After 0.5 hour the ratio of eseroline increased to 4%. Adjustment of the pH to 9.5 with HOAc (0.4 mL, 0.03 equiv.) and addition of 0.05 equiv isocyanate gave a 1/99 HPLC ratio of eseroline to product. The product (69 g) was isolated in 95% yield and 98% HPLC purity following water washing (300 mL), concentration of the THF phase, chromatographic purification on neutral alumina with DCM elution and recrystallization from diisopropyl ether.

EXAMPLE 14

(3aS,cis)-1,2,3,3a,8,8a-hexahydro-1,3a,8-trimethylpyrrolo [2,3-b ]indol-5-ol, cycohexylcarbamate (ester)

To a solution of physostigmine (75 g) in dry THF (700 mL), maintained under a nitrogen atmosphere at 8°–12° C., was added KOtBu (39.9 g) in portions over 1.0 hour while maintaining the temperature between 19°–23° C. After 0.5 hour the mixture was cooled to 10° C. and treated with glacial HOAc (17.1 mL, 1,1 equiv., pH=9.0–9.5). This mixture contained physostigmine (II) and eseroline (III) in a 1/99 HPLC ratio. Cyclohexyl isocyanate (54.5 g, 1.6, equiv) was added over 3.0 hours at 10°–20° C. During the addition of cyclohexyl isocyanate the pH was adjusted from 9.5 to 8.5 by the addition of glacial HOAc. The HPLC ratios of eseroline and (3aS-cis)-1,2,3,3a,8,8a-hexahydro-1,3a,8-trimethylpyrrolo[ 2,3-b]ind ol-5-ol cyclohexylcarbamate (ester) were:

| RNCO (equiv.) | pH | eseroline (% (HPLC) | cyclohexylcarbamate (% HPLC) |
| --- | --- | --- | --- |
| 0.3 | 9.5 | 68 | 32 |
| 0.6 | 9.5 | 39 | 61 |
| 0.9 | 9.5 | 13 | 87 |
| 1.1 | 9.5 | 9 | 91 |
| 1.3 | 9.5 | 20 | 80 |
| 1.5 | 8.5 | 8 | 92 |
| 1.6 | 8.5 | 0.6 | 99.4 |

The product (85.6 g) was isolated in 86% yield and 99.0% ttPLC purity following water washing (2×100 mL), concentration of the THF phase, and recrystallization from hexanes. It is to be understood that changes and variations may be made without departing from the spirit and scope of the invention as defined by the appended claims.

We claim:

1. A process for the preparation of a product of the formula

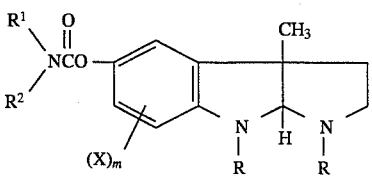

wherein

R is loweralkyl;

R¹ is hydrogen, loweralkyl, lowercycloalkyl, lowercycloalkylloweralkyl, lowerbicycloalkyl, aryl or arylloweralkyl;

R² is loweralkyl, lowercycloalkyl, lowercycloalkylloweralkyl, lowerbicycloalkyl, aryl or arylloweralkyl; or R¹ and R² taken together with the nitrogen atom to which they are attached from a 3,4-dihydro- 2(1H)-isoquinoline group;

X is loweralkyl, loweralkoxy, halogen or trifluoromethyl; and m is 0, 1 or 2;

which process comprises (a) contacting a compound of formula II

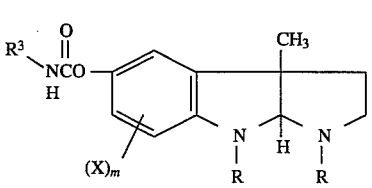

wherein R, X and m are as defined above and R³ is loweralkyl, with base followed by a carboxylic acid of formula

R⁵COOH wherein R⁵ is loweralkyl to afford a compound of formula III

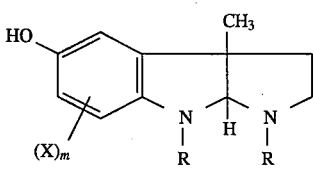

wherein R, X and m are as defined above;

(b) contacting, without isolating the compound of Formula III, the reaction mixture from step (a) either (1) with an isocyanate of the formula R²NCO and obtaining a product of the formula I wherein R¹ is hydrogen; or (2) with a compound of formula IV

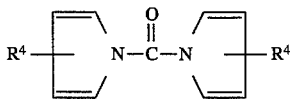

wherein R⁴ is hydrogen or loweralkyl in the presence of a carboxylic acid of the formula

R⁵COOH wherein R⁵ is as above to afford a compound of Formula V

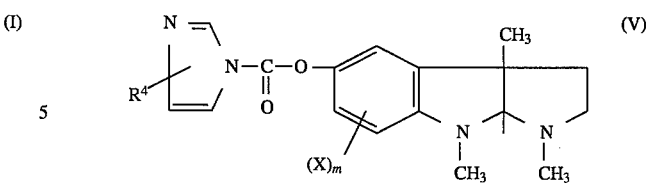

wherein R, R⁴, X and m are as above;

contacting the reaction mixture containing the compound of Formula V with a compound of the formula

R¹R²NH wherein R¹ and R² are as above; and isolating the product of Formula I.

2. The process of claim 1 wherein the base employed in step (a) is an alkyllithium.

3. The process of claim 2 wherein the alkyllithium is n-butyllithium.

4. The process of claim 1 wherein the base employed in step (a) is an alkali alkoxide.

5. The process of claim 4 wherein the alkali alkoxide is potassium butoxide suspended in a solvent.

6. The process of claim 1 wherein the base employed in step a is dissolved or suspended in a solvent.

7. The process of claim 6 wherein the solvent is an alkane or mixture thereof.

8. The process of claim 7 wherein the alkane is hexane or mixture thereof.

9. The process of claim 1 wherein a reaction solvent is employed.

10. The process of claim 9 wherein the solvent is an ethereal solvent.

11. The process of claim 9 wherein the ethereal solvent is selected from the group consisting of diethyl ether, 1,2-dimethoxyethane, 2-methoxyethyl ether, dioxane and tetrahydrofuran.

12. The process of claim 10 wherein the ethereal solvent is tetrahydrofuran.

13. The process of claim 1 wherein the carboxylic acid of steps (a) and (b) is acetic acid.

14. The process of claim 1 wherein the pH of the reaction medium of step (a) is adjusted to a value within the range of about 8.0 to about 13.0 by addition of a carboxylic acid.

15. The process of claim 14 wherein the pH is within the range of about 9 to about 10.

16. The process of claim 15 wherein the pH is about 9.5.

17. The process of claim 1 wherein the pH of the reaction medium of step (b) is adjusted to a value within the range of about 4.0 to about 6.

18. The process of claim 17 wherein the pH is within the range of about 4.5 to about 6.0.

19. The process according to claim 18 wherein the pH is about 5.5.

20. The process of claim 1 wherein R and R³ of the starting material is loweralkyl and X is hydrogen.

21. The process of claim 20 wherein R and R³ are methyl.

22. The process of claim 21 wherein the starting material is (3aS-cis)-1,2,3, 3a,8,8a-hexahydro- 1,3a,8-trimethylpyrrolo[2,3-b]indol-5-ol methylcarbamate (ester).

23. The process of claim 1 wherein R and X of the product are loweralkyl, hydrogen, respectively, and R¹ and R² form a 3,4-dihydro-2( 1H)-isoquinoline group.

24. The process of claim 23 wherein R is methyl.

25. The process of claim 24 wherein the product is (3aS-cis)-1,2,3,4,8,8a-hexahydro-1,3a,8-trimethylpyrrolo-[2,3-b]indol-5-yl 3,4-dihydro-2(1H)isoquinoline carboxylate.

* * * * *